United States Patent
Carew (10) Patent No.: US 11,559,466 B2
(45) Date of Patent: Jan. 24, 2023

(54) COVERING ASSEMBLY WITH COAGULANT COMPARTMENT AND USES THEREOF IN A BLOOD MONITORING/MANAGEMENT SYSTEM

(71) Applicant: Christopher A. Carew, Fair Oaks Ranch, TX (US)

(72) Inventor: Christopher A. Carew, Fair Oaks Ranch, TX (US)

( * ) Notice: Subject to any disclaimer, the term of this patent is extended or adjusted under 35 U.S.C. 154(b) by 0 days.

(21) Appl. No.: 17/026,106

(22) Filed: Sep. 18, 2020

(65) Prior Publication Data

US 2022/0023147 A1    Jan. 27, 2022

Related U.S. Application Data

(60) Provisional application No. 63/055,577, filed on Jul. 23, 2020.

(51) Int. Cl.
| | | |
|---|---|---|
| *A61J 1/20* | (2006.01) | |
| *A61J 1/14* | (2006.01) | |
| *A61M 1/00* | (2006.01) | |

(52) U.S. Cl.
CPC .......... *A61J 1/2027* (2015.05); *A61J 1/1412* (2013.01); *A61M 1/88* (2021.05); *A61M 1/882* (2021.05); *A61J 2200/00* (2013.01)

(58) Field of Classification Search
CPC .... A61J 1/2027; A61J 1/1412; A61J 2200/00; B65D 51/2828; B65D 51/2814;
(Continued)

(56) References Cited

U.S. PATENT DOCUMENTS

| | | | | |
|---|---|---|---|---|
| 4,540,413 A | * | 9/1985 | Russo | A61M 1/0001 604/320 |
| 5,185,007 A | * | 2/1993 | Middaugh | A61F 5/441 604/320 |

(Continued)

FOREIGN PATENT DOCUMENTS

| | | | |
|---|---|---|---|
| CN | 201070460 | | 6/2008 |
| DE | 10343668 A1 | | 4/2005 |
| DE | 202007003050 U1 | | 5/2007 |
| JP | 07-167716 A | | 7/1995 |
| KR | 20110072512 | * | 6/2011 |
| WO | WO 1997/027883 | * | 8/1997 |

OTHER PUBLICATIONS

English Translation of Specification and claims for Toyoshima et al. (WO 1997/027883). (Year: 1997).*

(Continued)

*Primary Examiner* — Ariana Zimbouski
(74) *Attorney, Agent, or Firm* — Denise L. Mayfield; Dykema Gossett, PLLC (57) ABSTRACT

Disclosed is a covering/lid assembly having a first compartment, a second compartment, or both. Each compartment will comprise a top side and a bottom side, the bottom side of the compartment comprising a frangible material. The first or second compartment may comprise a first material or a second material. The first or second material may comprise a flocculated red blood cell coagulant, or a red blood cell flocculent. The material within a compartment may be selectively released upon compressing a dimple and/or button located directly above the first and/or second compartment. A collection and/or biological waste management and disposal system is presented, comprising a lid/covering assembly as described and a collection container. The lid may include a perimeter having a threaded and/or snap-on assembly suitable for securely attaching the lid to a collection canister. The collection canister may comprise a red blood cell flocculent coating.

16 Claims, 7 Drawing Sheets

(58) Field of Classification Search
CPC ...... A61M 1/0098; A61M 1/88; A61M 1/882; A61L 11/00
See application file for complete search history.

(56) References Cited

U.S. PATENT DOCUMENTS

| | | | | |
|---|---|---|---|---|
| 5,238,582 | A * | 8/1993 | Hori | A61M 1/0096 210/206 |
| 5,549,585 | A * | 8/1996 | Maher | A61M 1/0001 604/317 |
| 5,686,074 | A * | 11/1997 | Stewart | A61K 33/06 424/736 |
| 5,945,004 | A * | 8/1999 | Ohira | A61L 11/00 210/710 |
| 10,401,347 | B2 | 9/2019 | Hemodus | |
| 2008/0293156 | A1* | 11/2008 | Smith | B01L 3/502 436/174 |
| 2010/0326151 | A1* | 12/2010 | Madigan | C05F 1/00 71/8 |
| 2011/0020425 | A1 | 1/2011 | Hen | |
| 2011/0163091 | A1 | 7/2011 | Hofmann et al. | |
| 2014/0183351 | A1* | 7/2014 | Cooks | H01J 49/0431 250/282 |
| 2018/0008757 | A1 | 1/2018 | Bannwart | |
| 2018/0196031 | A1* | 7/2018 | Carew | G01N 15/05 |
| 2019/0154658 | A1 | 5/2019 | Carew et al. | |
| 2019/0154659 | A1 | 5/2019 | Carew et al. | |
| 2019/0302096 | A1 | 10/2019 | Carew et al. | |

OTHER PUBLICATIONS

English Translation of Jae (KR 2011-0072512) Abstract and Specification. (Year: 2011).*
Nouri, S., et al., (2015) "Efficacy and Safety of Aluminum Chloride in Controlling External Hemorrhage: An Animal Model Study". Iran Red Crescent Medical Journal. Mar. 2015, 17(3).
Ratermann, A., et al., (1980), Journal of Agricultural Food Chemistry. 1980, 28, 2, 438-44.
Email from (Tatyana.Zalukaeva@uspto.gov) to Denise Mayfield (DMayfield@Dykema.com) and (Nicholas.Weiss@USPTO.gov), dated Apr. 6, 2022, 3:10 p.m., forwarding a Mar. 9, 2022, 4:28 p.m. email to Denise Mayfield.
International Application No. PCT/US2021/043041, Written Opinion and International Search Report of the Patent Cooperation Treaty (PCT), dated Nov. 9, 2021 (9 pages).
Definition of "Bellows", The American Heritage College Dictionary, Third Edition (1993), Houghton Mifflin Company, p. 126.
Definition of "Button", The American Heritage College Dictionary, Third Edition (1993), Houghton Mifflin Company, p. 192.
Definition of "Compressible", The American Heritage College Dictionary, Third Edition (1993), Houghton Mifflin Company, p. 286.
Definition of "Dimple", The American Heritage College Dictionary, Third Edition (1993), Houghton Mifflin Company, p. 286.
Definition of "Coagulant", Webster's New College Dictionary (1977), A Merriam-Webster G. & C. Merriam Company, p. 213.

* cited by examiner

COVERING ASSEMBLY WITH COAGULANT COMPARTMENT AND USES THEREOF IN A BLOOD MONITORING/MANAGEMENT SYSTEM

FIELD OF THE INVENTION

The present invention is related to the field of lids and/or coverings for a container.

BACKGROUND OF THE INVENTION

The containment and management of waste and other materials with potentially biohazardous materials, such as blood, requires careful handling. The presence of blood in fluids and other materials, such as materials generated during processing and/or procedures with animal and/or human bodies and/or corpses (e.g., surgery, taxidermy, corpse handling, processing and/or management (mortuary, morgue, hospital, veterinary office, taxidermy), tissue banks), requires that procedures and equipment be utilized to minimize contact and/or spillage generally of the fluid and/or waste. The problem of fluid/waste spilling and contact creates significant risk of exposing a patient, attending clinical personnel, and a surrounding surgical environment to blood contaminants. Existing collection vessels/containers used in materials collection and disposal do not effectively control for liquid/waste contaminant exposure, due at least in part to the fluid state in which any blood present in the collected material exists.

Containers for collecting biologically hazardous materials, particularly those materials collected from surgical procedures, may include a lid that includes a port that must be manually opened by a user, and manually emptied by the user, in order to dispose of the liquid waste contents. This procedure creates risk of contaminating the user performing the disposal activity, risk of contaminating others within the immediate area where the contents are being disposed of, and risk of contaminating the area in general where the procedure is being performed. Safer disposal methods for handling and discarding liquid or semi-liquid waste materials are needed, especially in the medical arts, to guard against these potential and significant health safety risks and/or other hazards.

The liquidity of a collected material is associated, at least in part, with the liquid state in which any blood in the material remains for several hours under standard room temperature and collection conditions. Any blood present may remain in a liquid state for much longer time periods, depending on what other materials are present. Techniques for quickly and easily reducing the liquidity of collected material, particularly biohazardous materials, remain largely underdeveloped to meet current needs.

Blister packaging sub-assemblies or "blister packs", have been used for convenient packaging of a variety of consumer products, such as chewing gum, throat lozenges, certain medications, and the like. As used in this sense, a "blister pack" is understood to relate to a pre-formed plastic and/or foil packaging used for small consumer product goods, foods and pharmaceuticals. (chewing gum, etc.). The blister pack typically will provide a cavity or pocket created with a formable web or an aluminum foil or plastic on one side, and a paperboard or other less conformable back wall or seal on the other side. The product may be easily expelled and retrieved by a user by exerting force on the back wall to expel the product through the aluminum foil or plastic compartment, and into a users' hand, for example. In typical blister packs, the content of a blister pack "chamber" compartment will be released upon a user applying direct force against the back wall of the "pack", with the back wall remaining intact.

Generally, upon exerting a direct pressure to the back wall of the blister pack, the weakest part of the front wall or encasing layer of the blister "pack" assembly will be thrust out of the compartment, as the front wall material is perforated by the product contained in the "pack" compartment. When pressure is applied to the blister, the backing seal ruptures, and the contents of the blister are ejected through the tear in the backing seal.

Blister pack units are described in German patent application DE10343668A1, which relates to a leak-tight blister pack for medication. In another example, German patent application DE202007003050U1 relates to a blister pack for a liquid substance that is released into the external environment by diffusion.

The medical arts remain in need of improved devices, materials and methods for handling and safely managing the disposal of liquid or semi-liquid materials having blood or blood components, and that avoid and/or minimize user contact.

SUMMARY OF THE INVENTION

The present disclosure provides a solution to these and other problems existing in the art.

In a general and overall sense, the present invention provides materials, devices, and systems for safely managing and disposing of potentially health hazardous materials that may include a fluid component, such as those materials collected during or following a laboratory, medical or other procedure. In particular, devices and methods for processing and disposal of materials collected during a surgical procedure, that are at risk of containing blood or blood products, are presented. The disclosed devices and methods include a covering assembly, such as a lid, cover, and/or cap, that provides a tool which permits an enhanced safety, contact-free disposal solution for potentially biohazardous materials. In this sense, a waste collection and biohazard disposable system is provided.

The device, in one embodiment, comprises a covering and/or lid assembly comprising a first compartment containing a coagulant material capable of coagulating a blood component (red blood cells), the first compartment having a top side and a bottom side, wherein the top side comprises a compressible button or dimple. In this embodiment, the compressible button or dimple will be preferably situated above a frangible layer located on the bottom side of the first compartment, wherein the frangible layer, upon rupture, will release the coagulant material and function to coagulate and/or gelatinize blood components in a material, such as red blood cells.

In some embodiments, the coagulant material is selectively released from the compartment upon rupture of the frangible layer/covering, and into a container or other receptacle. Thus, in operation, when the compressible button or dimple is compressed, the coagulant, in particular a blood coagulant, will be selectively released. Any blood component in the container and/or compartment will thereafter quickly form a coagulated semi-solid, gel-like state, thus permitting an essentially spill-free, more easily disposable material solid and/or semi-solid mass.

In other embodiments, the comprises a covering and/or lid assembly comprising a second compartment containing a red blood cell flocculent material, capable of flocculating a blood component (red blood cells), the second compartment having a top side and a bottom side, wherein the top side comprises a compressible button or dimple. In this embodiment, the compressible button or dimple will be preferably situated above a frangible layer located on the bottom side of the compartment, wherein the frangible layer, upon rupture, will release the red blood cell flocculent material and function to flocculate red blood cells by associating with the surface of the red blood cells, thereby inhibiting blood coagulation.

Virtually any coagulant capable of coagulating blood, or more specifically, red blood cells, and even more specifically, flocculated red blood cells, is a material that may be used in the present devices/lids/caps.

Table 1 presents examples of red blood cell (RBC) flocculants. RBC's that have been flocculated (not coagulated) with these flocculants, may be further coagulated to provide a solid or semi-solid mass, upon being exposed and/or combined with a coagulant as provided with the present devices and methods.

opening, such as to the top opening of a collection vessel or device. In some embodiments, the cap/lid/cover lid assembly will be configured to include a blister pack as described above, and will contain the blood coagulant within the blister pack as part of a lid assembly. The lid assembly, in some embodiments, will be configured so as to attach securely to an opening of a collection vessel of choice.

In some embodiments, the blister pack may comprises two films which in turn may be made up of several layers of different or identical materials. The films may be made of plastics and/or metal, e.g. aluminum, while other materials such as paper or the like may theoretically also be used, or used in addition. The two films are, in particular, a base layer or base film (support) and a cover layer or cover film (cover).

In the base film or support there may be one or more wells or depressions for holding the liquid, into which the liquid, particularly a pharmaceutical formulation, is introduced. The cover film or the cover is then placed on the base film or support and fixed or attached thereto, and this is done, for example, at the edges or in a connecting region, particularly

TABLE I

| Chemicals | Descriptions |
| --- | --- |
| Gelatin | A solution of electrostatic charged poly-peptides having a wide range of molecular weight. Literature indicates gelatin is able to increase RBC aggregation after adsorption on a RBC surface. |
| Dextran 80 + CaCl$_2$ | Literature indicates that Dextran 80 plus a divalent cation like Ca$^{2+}$, and Ba$^{2+}$ will increase aggregation of RBCs |
| Acid Treatment | The isoelectric point of blood is at pH = 4.75-5. The pH change of blood samples to less than 4.75 will convert RBCs from negative to positive surface charge. |
| Polyethylenimine (PEI) with different molecular weight | PEI is a polymer composed of large number of positively charged amine groups, which is expected to attract RBCs to cause RBC settlement. |
| Polyacrylamide (PAM) with different molecular weight | PAM is widely used as a flocculants for water treatment. It can be configured to either positive or negative charge. Positively charged PAM is toxic to aquatic wildlife. |
| Aluminum sulfate (Alum) | Alum is positively charged at neutral pH. |
| Polydiallyldimethylammonium chloride (PolyDADMAC) with different molecular weight | PolyDADMAC is a positively charged water-soluble polymer |

RBCs present in a fluid containing blood become bound to each other in the presence of an RBC flocculent, and in this manner form heavier particles that settle within the container/bottle/tube/collapsible bag or other vessel within which a sample/material is collected. Once the flocculated RBCs in a collected biological material settle, the flocculated settled RBCs may be easily re-dispersed, and do not coagulate and/or do not form a solid mass that may be easily and safely disposed of. Therefore, these may be coagulated by providing one or more appropriate coagulants to the flocculated settled or dispersed red blood cells.

In some embodiments, the flocculated RBC's are polydiallyldimethylammonium chloride (PolyDADMAC) flocculated RBC's. Virtually any type of flocculated RBC material may be processed to create a solid or semi-solid mass in the practice of the present invention. Examples of RBC flocculants include polymeric RBC flocculants and non-polymeric RBC flocculants. Non-polymeric RBC flocculants may include acids, such as HCl or other acid molecule.

Selection of an appropriate coagulant requires that the coagulant be capable of forming a solid or semi-solid mass from a liquid comprising red blood cells that have been flocculated.

Kits are provided wherein a blood coagulant is packaged as part of a lid/cap/cover assembly, and configured to securely attach (screw, snap, etc.) to a collection vessel in flatly abutting surface regions, preferably by adhesion, heat-sealing, welding or the like.

The blister pack may be sealed by an inert compound that minimally interferes with analysis of the blood, coagulant, or other chemicals to be introduced in the experimentation medium. In order to allow the blister to rupture under pressure, a frangible seal is often provided around at least part of a perimeter of the blister cavity. Such frangible seal technologies allow relatively controlled release of reagents, whilst eliminating the need for complex fluid handling systems or external piercing means.

The sealing material for the blister pack may be a plastic film made from a material comprising, for example, polyethylene, polypropylene, polybutylene, polyvinyl chloride, or a combination thereof. The sealing material for the blister pack may also be a layer of aluminum foil.

The blister cavity or pocket may be made from a formable web, usually a thermoformed plastic such as PVC, PVDC, Polychlorotrifluoroethylene (PCTFE), or cyclic oledfin copolymers (COC) or polymers (COP). These aforementioned materials may be combined with polypropylene (PP), polyethylene (PE), or glycol-modified polyethylene terephthalate (PETg) to add more protection.

Blood Coagulant: Various types of blood coagulants may be used with embodiments of the present invention. These may include salts formed from inorganic compounds such as Cu (II), Ag (I), Fe (II), Fe (III), Ti (IV), and Ni (II). The coagulant may be aerosolized, and/or applied in a powder form, such as the compound known commercially as m-doc® Active, a calcium sodium salt of micro-dispersed oxidized cellulose that is an ingredient in a bleeding control spray sold under the name QUICKSTOP!®. An effective coagulant may comprise a solution of any of the following compounds: methanol; poly-aluminum chloride; silver nitrate; copper (II) sulfate, copper (II) bromide; ferric sulfate; ferric subsulfate; ferric chloride; aluminum sulfate; or zinc sulfate. The flocculated red blood cell coagulant may be provided in the form of a powder, a tablet, or a liquid as part of the present devices and methods employing the devices. Table II provides examples of the flocculated red blood cell coagulants:

TABLE II

| Chemicals | Descriptions |
|---|---|
| aluminum chloride | |
| styptic powder | |
| copper (II) sulfate alum | |
| potassium aluminum | |
| potassium ferrate | |
| ferric or ferrous sulfate | |
| ferric subsulfate | |
| ferric chloride | |
| aluminum sulfate (Alum) | |
| methanol | |
| zinc sulfate | |

Covering/Lid Assembly for Canisters, Collection Bags and Containers: Collection devices including canisters, collection bags and containers suitable for the collection and visual estimation of blood loss may be used with the covering and/or lid assemblies provided in the present disclosure.

In some embodiments, the lid/covering assembly may include one or more than one frangible compartments. One of the frangible compartments will comprise a coagulant that will effectively coagulate flocculated red blood cells in a fluid.

In another embodiment, the lid/covering assembly will comprise a first frangible compartment comprising a coagulant that will effectively coagulate flocculated red blood cells in a fluid, and a second frangible compartment comprising a red blood cell flocculent. This embodiment of the lid/covering assembly is envisioned for use with a collection or other container that has an interior that has not been treated to include a red blood cell flocculent. As part of a blood loss assessment device, the lid having these two frangible compartments will be employed together with a collection device that has not been previously treated to include an interior surface comprising a coating of a red blood cell flocculent. Prior to or during collection of a fluid into the container, the red blood cell flocculent in the second frangible compartment will be released into the interior of the collection container. The presence of the red blood cell flocculent will allow any red blood cells in the collected material/fluid to settle in the container, and form a discernable settled red blood cell level. However, the settled flocculated red blood cells may be readily dispersed if the contents of the container are disturbed, and there is no solid coagulation. In order to transform the flocculated red blood cells into a more easily disposable solid and/or semi-solid mass, the flocculated red blood cell coagulant material contained in the second frangible compartment of the lid assembly may be securely released into the interior of the container, without opening the container or removing the lid/covering assembly. In this manner, a safe, secure, contact-free assembly and device is provided for both assessing settled red blood cell levels (and calculating blood volume therefrom) in a material, and disposing of the collected material having or suspected to contain blood and/or red blood cells, in a single assembly, without exposing the contents to the environment or the user.

The lid assembly in either embodiment may be configured to have a circumference that permits the lid assembly to securely and snugly fit over the top or opening of a collection device, such as a biological fluid collection device. The biological fluid collection device may take the form of such devices as those described in U.S. Pat. No. 10,401,347 and Patent Publication Nos. 2019/0302096A1, 2019/0154659A1, and 2019/0154658A1, and corresponding patents and patent applications outside of the United States, that include as a component a red blood cell flocculent provided on a surface of the collection container, such as a surface coating of a red blood cell flocculent on the inside surface of a container. The container may be in the shape of a canister, an envelope or bag, or other configuration onto which a coating of a red blood cell flocculent material may be provided. These patents and patent applications are specifically incorporated herein by reference.

In summary, the present covering and/or lid assembly may be used together with a collection device, such as a canister or collection bag or sleeve, that is preferably sufficiently transparent or at least opaque so as to permit the visual detection of a level of material, such as a level of sedimented, flocculated red blood cells (settled RBC's, not coagulated blood) within the collection device. The collection device can be of a solid or flexible material, such as a hard plastic or glass, or a flexible material, such as a plastic or other non-rigid material suitable for containing a liquid and/or semi-liquid state material comprising or suspected to comprise blood. Such liquid and/or semi-liquid material comprising blood or suspected to comprise blood, includes a liquid medical waste material comprising blood.

These descriptions are provided by way of example and are not intended to provide limitation of potential embodiments envisioned for use and practice of the present devices.

BRIEF DESCRIPTION OF THE DRAWINGS

FIG. 1 illustrates an embodiment of the covering and/or lid assembly disclosed herein.

FIG. 2 illustrates an embodiment of the collection system disclosed herein.

FIG. 3 illustrates a plan view of one embodiment of the covering assembly and/or lid top portion disclosed herein.

FIG. 4 illustrates a plan view of one embodiment of the covering assembly and/or lid bottom portion disclosed herein.

FIG. 5 illustrates another embodiment of the covering assembly disclosed herein.

FIG. 6 illustrates a plan view of another embodiment of the covering assembly top portion disclosed herein.

FIG. 7 illustrates a plan view of another embodiment of the covering assembly bottom portion disclosed herein.

DETAILED DESCRIPTION OF THE PREFERRED EMBODIMENT

Unless defined otherwise, all technical and scientific terms used herein have the same meaning as commonly understood by one of skill in the art to which the disclosure pertains. Although any methods and materials similar to or equivalent to those described herein can be used in the practice or testing of the present technology, the preferred methods and materials are described herein.

As used here, the term "flocculent" is intended to mean a molecule that has a cationic charge that is capable of facilitating the coalescence of RBCs in a fluid at room temperature, and form a settled RBC mass with less than 30 minutes at room temperature without centrifugation.

Reference to an element by the indefinite article "a" or "an" does not exclude the possibility that more than one element is present, unless the context clearly requires that there be one and only one element. The indefinite article "a" or "an" thus usually means "at least one."

As used herein, "patient" or "subject" means an individual having symptoms of, or at risk for, cancer or other malignancy. A patient may be human or non-human and may include, for example, animal such a horse, dog, cow, pig or other animal. Likewise, a patient or subject may include a human patient including adults or juveniles (e.g., children). Moreover, a patient or subject may mean any living organism, preferably a mammal (e.g., human or non-human) from whom a blood volume is desired to be determined and/or monitored from the administration of compositions contemplated herein.

As used herein, "waste" means any mixture in any amount comprising blood and/or a coagulant of any type that is enclosed in a receptacle sealed by any embodiment of the covering assembly.

As used herein, "blood coagulant enhancing substance" means any of the variously named compounds that may be used as a blood coagulant.

As used herein, "about" means within a statistically meaningful range of a value or values such as a stated concentration, length, molecular weight, pH, sequence identity, timeframe, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The following examples are presented to demonstrate preferred embodiments of the invention.

EXAMPLE 1

Covering/Lid Assembly

Figure 1:
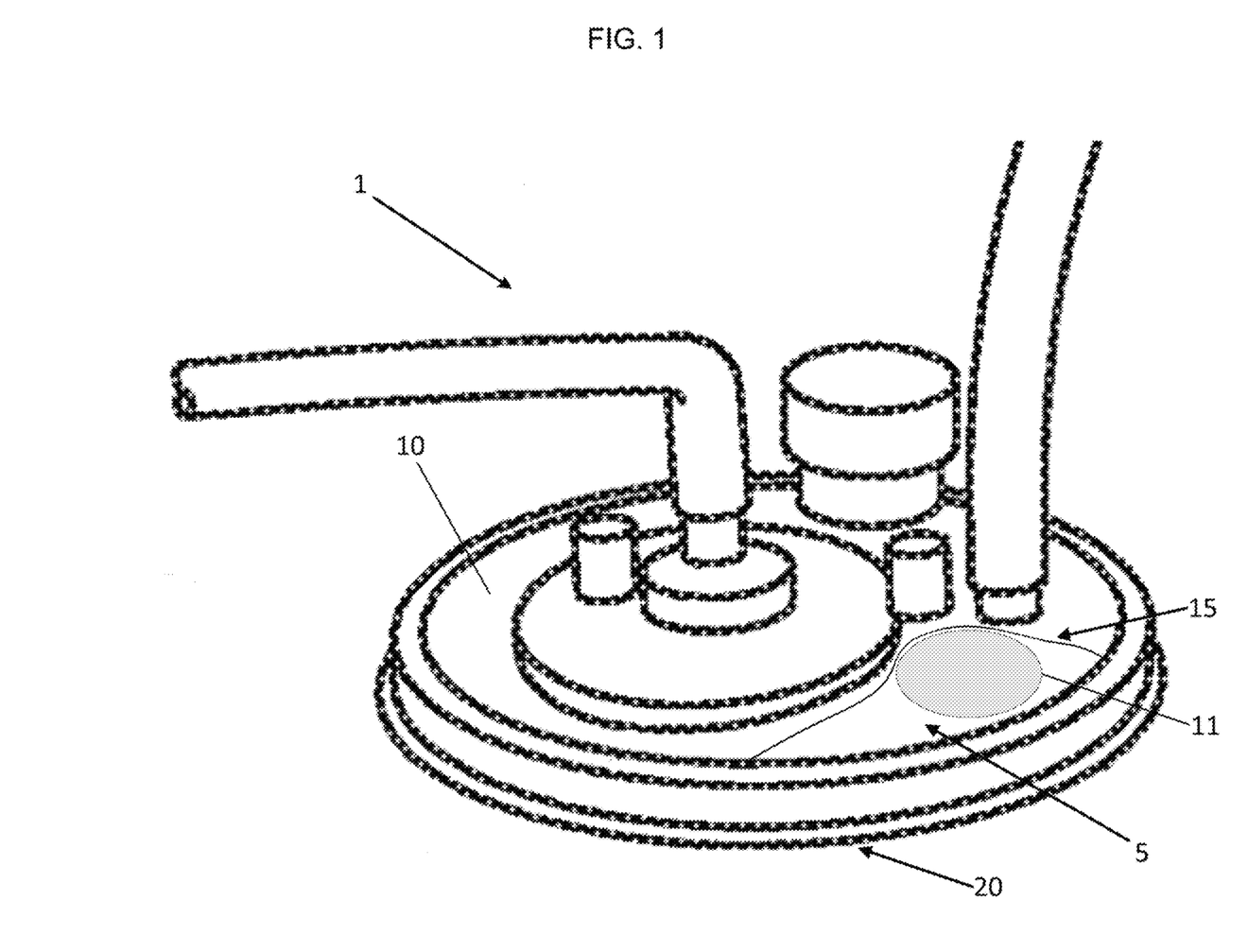
Figure 3:
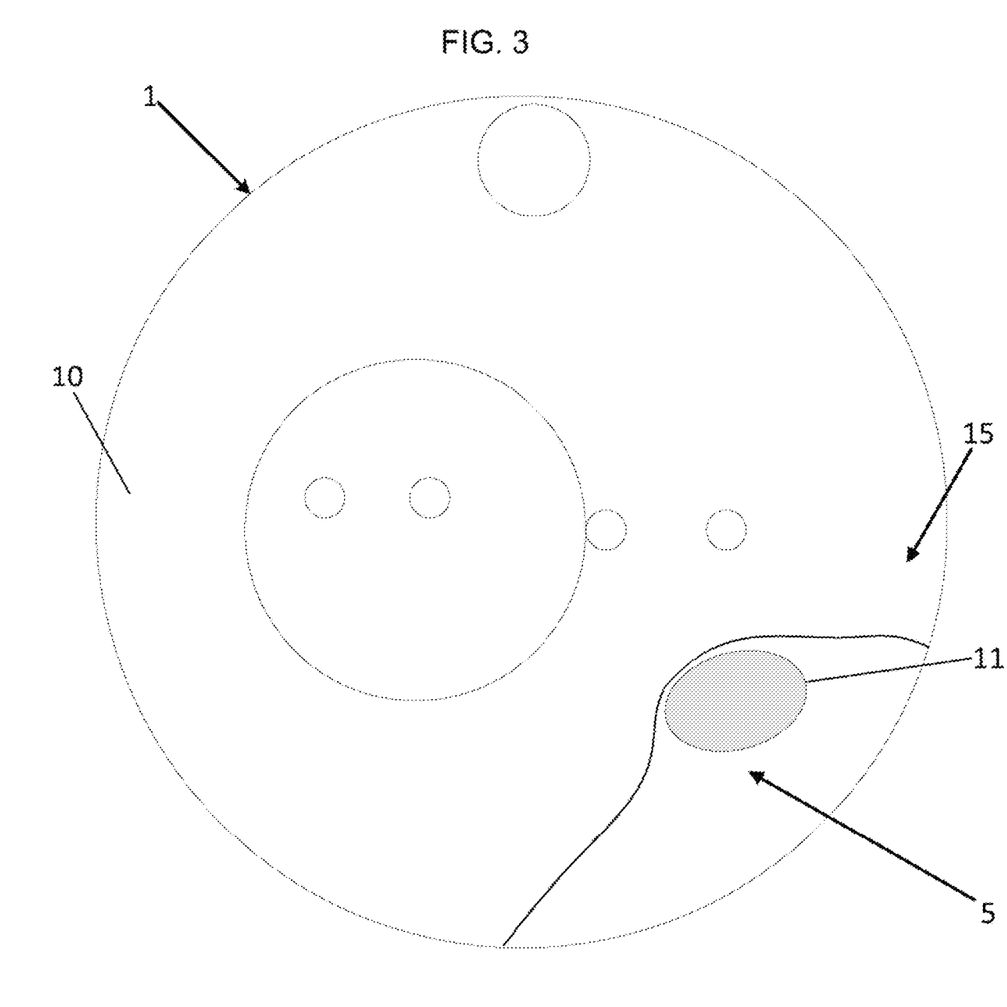

The present example presents a description of one embodiment of the covering assembly/lid 1. The covering assembly/lid is illustrated in FIGS. 1, 3, and 4.

The covering assembly/lid 1 includes a top portion 10 and a bottom portion 20, and further includes a frangible compartment 5 situated on a first surface 25 of the covering assembly bottom portion 20. Covering assembly/lid 1 may comprise a transparent plastic material, such as a polyethylene or a polypropylene. The frangible compartment 5 contains a blood coagulation enhancing substance 50 that is selectively releasable from the frangible compartment 5.

Figure 4:
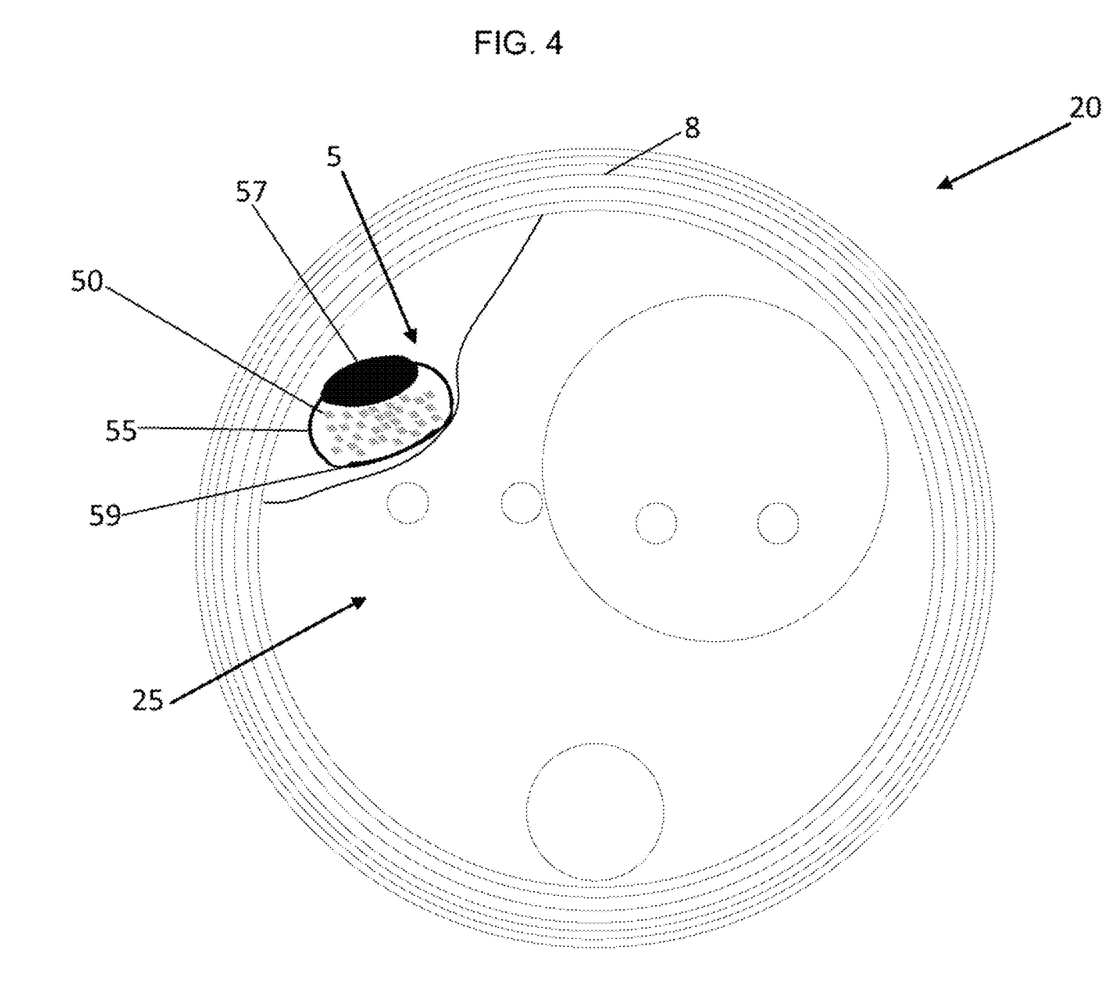

In one embodiment, the blood coagulation enhancing substance 50 may be powder, as illustrated in FIG. 4. However, blood coagulation enhancing substance 50 may be in the form of a powder, a tablet, or a liquid, and may be selected from any of the aforementioned blood coagulant compounds previously listed. The blood coagulation enhancing substance 50 may be enclosed in a frangible compartment 5. The frangible compartment may be provided as a blister pack, the blister pack comprising a release side comprising a frangible material, such as an aluminum, tin, or other foil, aplastic, or other frangible material. The blood coagulation enhancing substance 50 may be contained within the blister pack. Alternatively, the blood coagulation enhancing substance may be packaged in a box, a bottle, a tray, a cartridge, or a card.

Covering assembly/lid 1 may also include a coupling adapter 8 along a perimeter 12 of the covering assembly 1. The coupling adapter 8 with a threaded connection that is suitable for attaching the covering assembly 1 onto a canister 30 to provide a fluid-tight seal. Coupling adapter 8 may comprise, for example, a threaded connection, or a screw connection, or a locking connection. As shown in FIG. 1, the covering assembly/lid 1 may include a compressible button or dimple 11, that is comprised of a non-frangible material, on a first surface 15 of the covering assembly top portion 10. The compressible button or dimple 11 in some embodiments is situated above the frangible compartment 5, and when a compressive force (such as pushing the dimple/button "in"), is applied by a user to the compressible button or dimple 11, the blood coagulation enhancing substance 50 is released from the delivery compartment 55, as the frangible layer of the compartment opens/breaks, for example, by the force exerted by a substance contained within the frangible compartment against the frangible layer and/or the pressure exerted upon pressing the button or dimple 11.

In one embodiment, and as shown in FIG. 4, a first frangible compartment 55 comprises a non-frangible top layer 57 and a bottom frangible layer 59. Application of pressure to the non-frangible layer 57 results in force being applied to bottom frangible layer 59, causing the frangible layer to break or tear. The break and/or tear of the frangible layer in turn results in the release of the blood coagulation enhancing substance 50, and into an enclosed collection device.

The compressible button and/or dimple 11 located on the non-frangible top layer 57 may be comprised of one or more plastic materials that are pliable and able to be bent by an applied pressure. The bottom frangible layer 59 may comprise a layer of aluminum film or other material that will be broken/torn by an applied pressure to the button and/or dimple. The applied pressure may originate from, for example, a user pressing the button and/or dimple in or down, thus creating air pressure to be applied against the interior of the frangible compartment and through the bottom frangible layer 59.

EXAMPLE 2

Collection System

Figure 2:
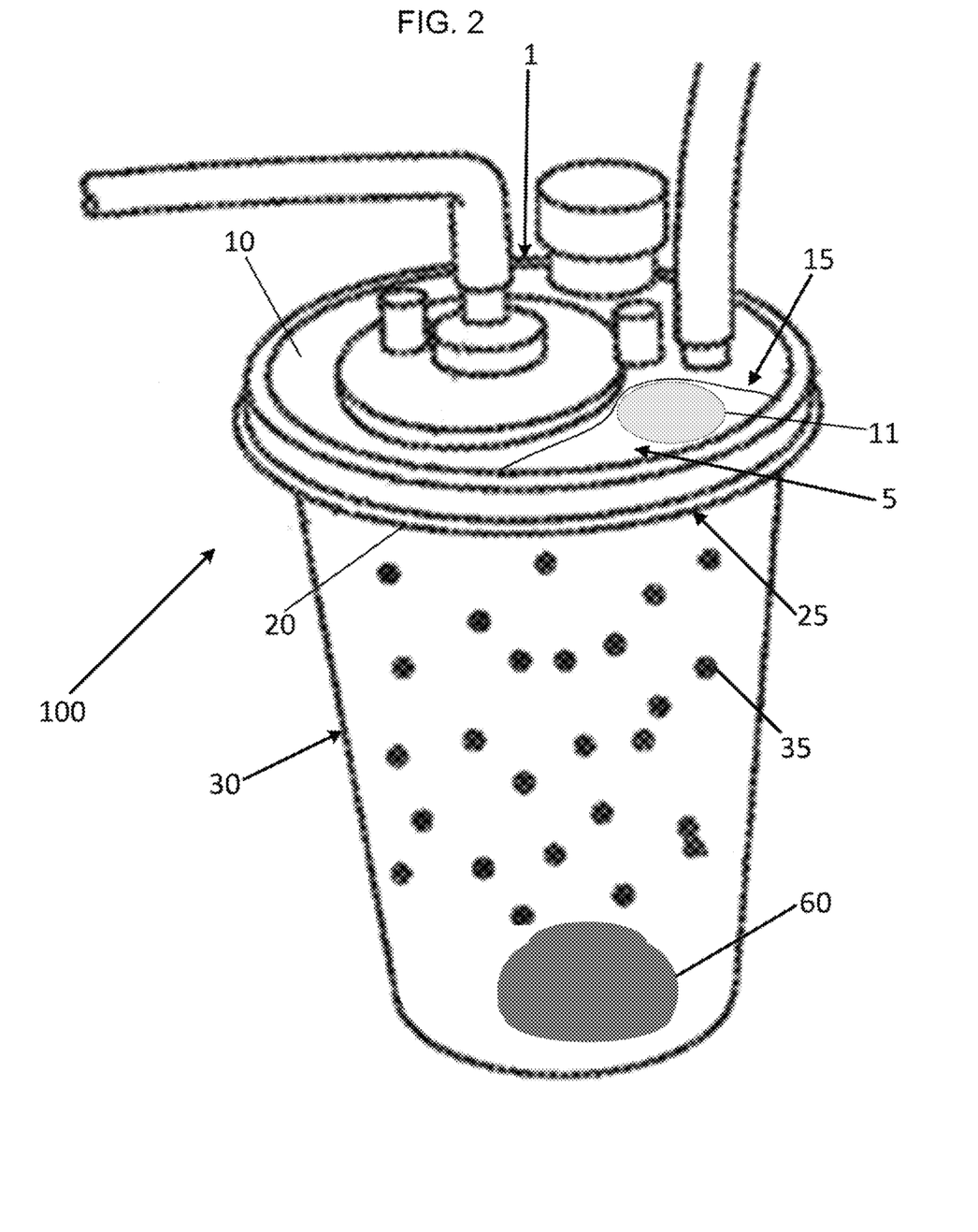

The present example presents the collection system 100 of the present invention. The system is illustrated in FIG. 2. The collection system 100 includes a collection vessel that may connect to a covering and/or lid assembly 1. The covering and/or lid assembly 1 includes a top portion 10 and a bottom portion 20, and further includes a frangible chamber 5 situated on a first surface 25 of the covering assembly bottom portion 20.

Frangible chamber 5 contains a blood coagulation enhancing substance 50 that is selectively releasable from the frangible chamber 5. The blood coagulation enhancing substance 50 may be enclosed in a compartment 55, which may be a blister pack. The blister pack is made up on one surface a frangible material, such as a surface comprising plastic and/or an aluminum foil material. The covering and/or lid assembly 1 has a coupling adapter 8 along a perimeter 12 of the covering assembly 1, and the coupling adapter 8 with a threaded configuration that is suitable for attaching the covering assembly 1 onto the top opening of a canister 30 to provide a secure, fluid-tight closing.

Covering assembly 1 may include a compressible button or dimple 11 on a first surface 15 of the covering assembly top portion 10. The compressible button or dimple 11 may be situated above the detachable chamber 5. When the compressible button or dimple 11 is compressed, the button or dimple 11 pushes air that engages the frangible compartment 55, which causes the blood coagulation enhancing substance 50 within the delivery compartment 55 to be released into the adjacent canister 30. Canister 30 a fluid sample 60 including fluids such as settled RBCs and other media to be disposed. When the blood coagulation enhancing substance 50 released from delivery compartment 55 and is mixed with the fluid sample 60 in canister 30, the waste components of fluid sample 60 coagulate and prevent formation of a biohazard. Coagulation of fluid sample 60 by the blood coagulation enhancing substance 50 may take place, for example, in the presence of a flocculent 35.

Waste is collected in collection system 100 a single time and then the entire system and waste contents are discarded. Collection system 100 is self-contained, does not require cleanup for disposal of the contents therein, and thereby prevents creation of a biohazard. No additional solution or other cleaning is required for disposal of the contents in collection system 100.

Collection system 100 may be propped up or set up on a stand, such as a tower for IV drip containers. Each time a medical procedure is completed and fluids are collected in the collection system 100, the enclosed system and the contents therein are disposed. A new collection system is then substituted in place of the used collection system, and the new system is used to process additional waste. The canister 30 may be, for example, a flocculated container, having flocculent 35. Examples of flocculated containers are described in U.S. Patent Publication Nos. 2019/0302096A1, 2019/0154659A1, 2019/0154658A1 and U.S. Pat. No. 10,401,347, which are hereby incorporated by reference.

Collection system 100 also provides for estimation of blood volume in the contents within collection vessel 30.

EXAMPLE 3

Contact-Free Biological Material Collection and Disposal System

The present example presents a contact-free system for collecting and disposing of biologically hazardous materials that minimizes user handling. The system provides for collection and processing of a fluid suspected to include or including a biological material, such as blood, into a collection canister, assessing a volume of blood that is present in the collected material, and transforming the content of the container into a readily disposable solid and/or semi-solid mass in the container, without removal of the covering/lid assembly.

Figure 5:
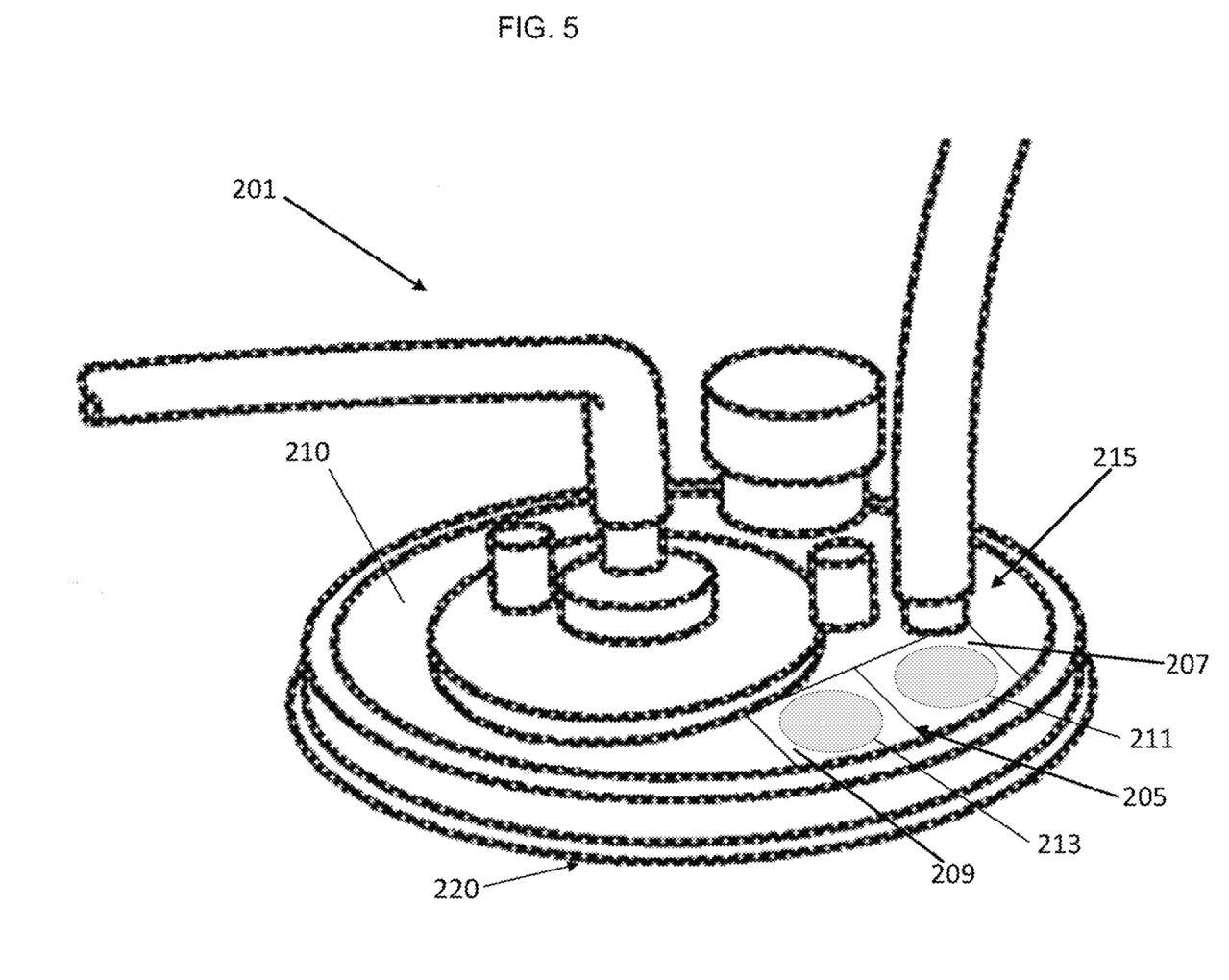
Figure 6:
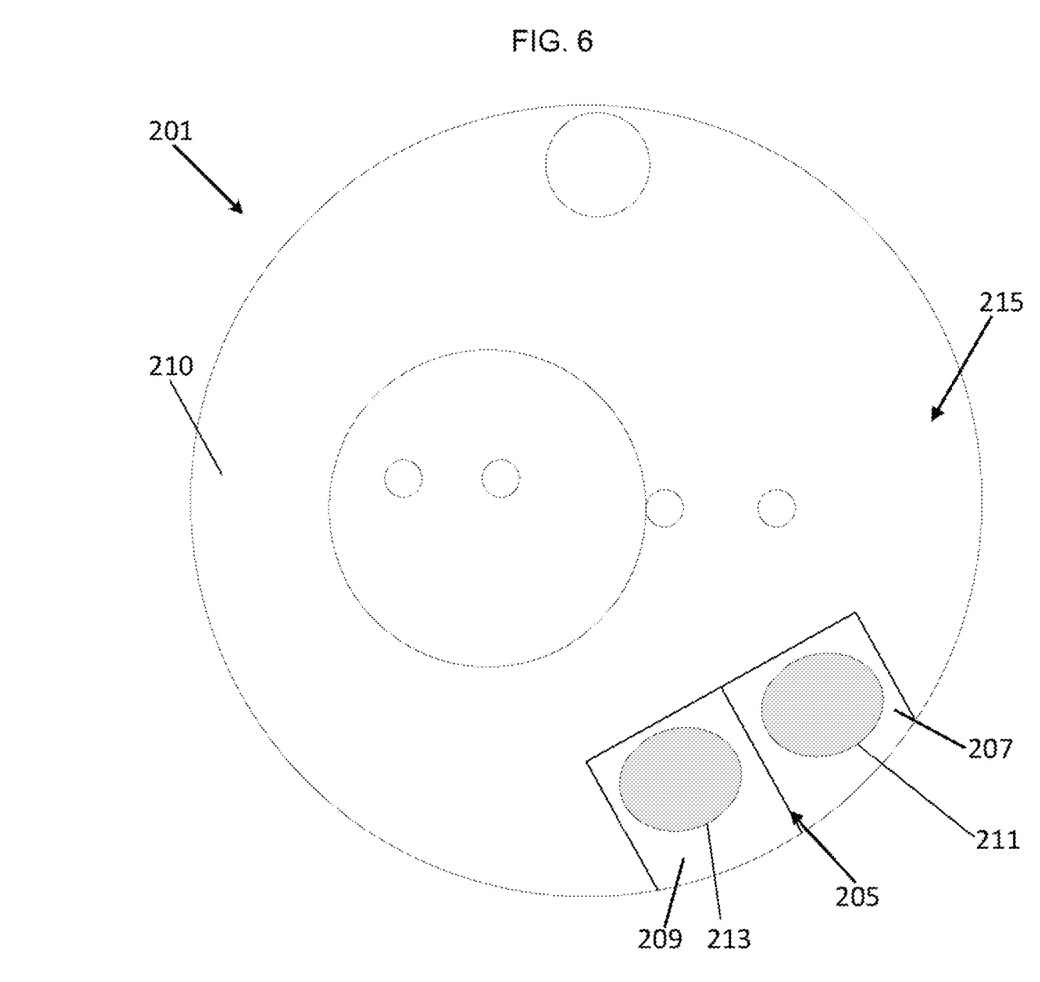
Figure 7:
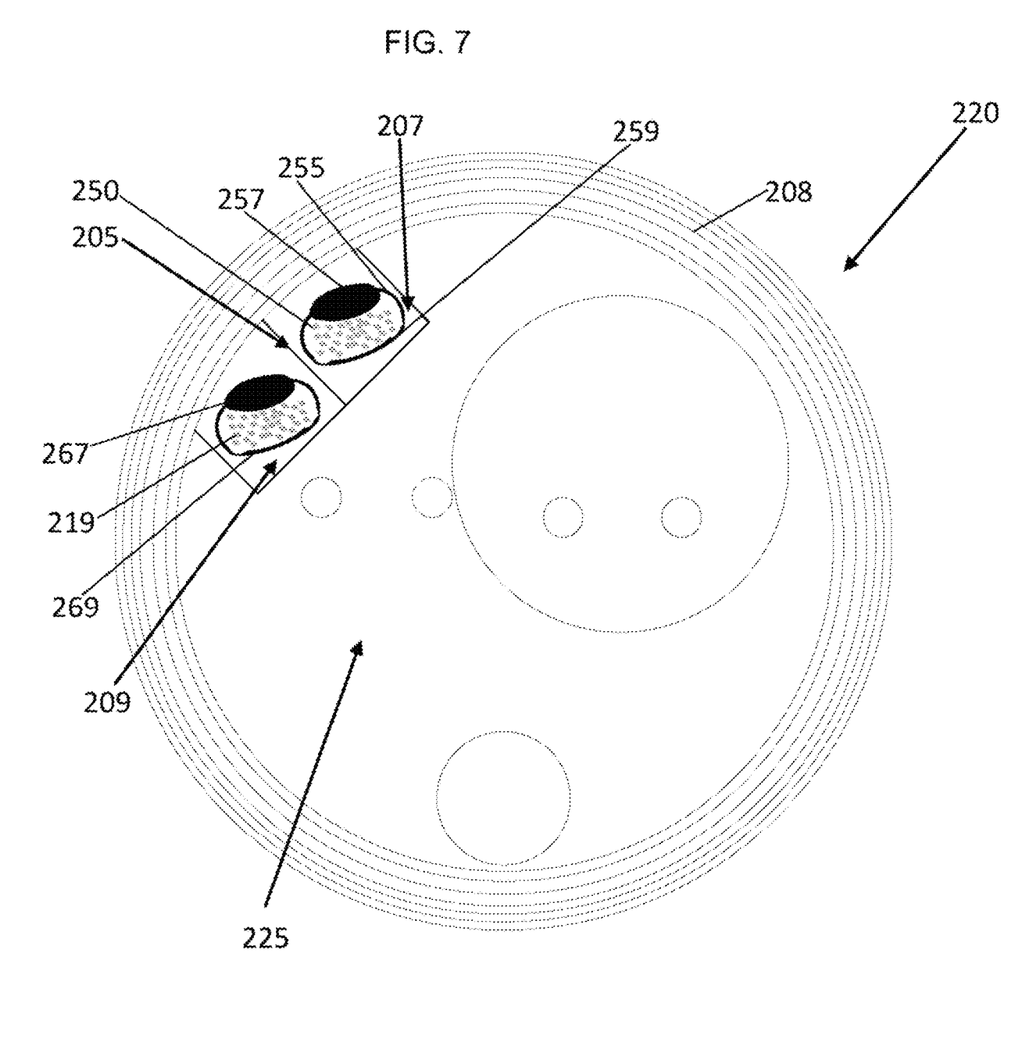

An embodiment of the covering assembly is illustrated in FIGS. 5, 6, and 7. Covering assembly 201 includes a top portion 210 and a bottom portion 220. A first chamber includes a frangible material layer 205 situated on a first surface 225 of the covering assembly bottom portion 220.

The covering assembly and/or lid 201 may comprise a plastic material, such as a polyethylene or a polypropylene.

The frangible material layer 205 will be positioned at a bottom side of s first compartment 207. The first compartment may contain a red blood cell flocculent material or a blood coagulant material 250. A first button/dimple 211 will be located directly above the frangible chamber, and upon pressing the button and/or dimple, the material in the compartment will apply a force against the frangible material surface that breaks the surface, thus expelling the material into an interior chamber of a collection container. Thus, as the surface of the first frangible chamber is breached from the application of the force, the material is released into the container where it will mix and contact with the fluid contents.

A second compartment 209 may also be provided, this compartment comprising a preferred material, such as a red blood cell flocculent or blood coagulant (capable of transforming flocculated red blood cells into a solid and/or semi-solid mass). This solid and/or semi-solid mass may then be easily disposed of, without risk of splashing or spilling onto another person or in the surrounding area.

A second button/dimple 213 defining one side (the top side) of the second compartment, will be located directly above a second frangible layer, and upon pressing the second button and/or dimple, the material within the second compartment (such as a red blood cell flocculent or a flocculated red blood cell coagulant material) will be forced through the frangible layer of the compartment and into a collection device interior.

The first button/dimple 211 and the second button/dimple 213 may each be substantially level with first surface 215 of the covering assembly top portion 210 to improve the compactness of covering assembly 201, and allow for stackable storage for more than one covering assembly 201. This may also ensure that the first button/dimple 211 and the second button/dimple 213 do not become exposed to force that would press upon them upon packaging and shipping of the covering assembly 201.

The flocculated red blood cell coagulant substance may be a powder, or other form, such as a tablet, or a liquid. The flocculated red blood cell coagulant, red blood cell flocculent, or both, may be enclosed in a blister pack within the first compartment or the second compartment, for example, within a pack made of a plastic and/or aluminum foil. The flocculated red blood cell coagulant or red blood cell flocculent may alternatively be packaged in another material such as, for example, a box, a bottle, a tray, a cartridge, or a card, within the first compartment or second compartment, or both compartments.

Covering assembly 201 also includes a coupling adapter 208 along a perimeter 212 of the covering assembly 201, and the coupling adapter 208 with a threaded connection that is suitable for attaching the covering assembly 201 onto a canister 230 to provide a fluid-tight seal. Coupling adapter 208 may comprise, for example, a threaded connection, or a screw connection, or a locking connection.

Covering assembly 201 may be interchangeably used with the collection system 100 previously described herein.

The examples set forth above are provided to give those of ordinary skill in the art a complete disclosure and description of how to make and use the embodiments of the methods for prediction of the selected modifications that may be made to a biomolecule of interest, and are not intended to limit the scope of what the inventors regard as the scope of the disclosure. Modifications of the above-described modes for carrying out the disclosure can be used by persons of skill in the art, and are intended to be within the scope of the following claims.

It is to be understood that the disclosure is not limited to particular methods or systems, which can, of course, vary. It is also to be understood that the terminology used herein is for the purpose of describing particular embodiments only, and is not intended to be limiting.

A number of embodiments of the disclosure have been described. Nevertheless, it will be understood that various modifications may be made without departing from the spirit and scope of the present disclosure. Accordingly, other embodiments are within the scope of the following claims.

I claim:

1. A covering and/or lid assembly for a container, said covering and/or lid assembly comprising:
a first compartment, said first compartment comprising a first chamber, a compressible button or dimple, said compressible button or dimple being situated above the first chamber, and a frangible covering being situated below the first chamber;
wherein a blood coagulant material is contained in the first chamber;
wherein the blood coagulant material is selectively released from the first chamber into the container upon compression of the button or dimple, and the blood coagulant material is configured to form a coagulated mass of blood in the container to provide spill-free disposal of blood;
a second compartment, said second compartment comprising a second chamber, a second compressible button or dimple, said second compressible button or dimple being situated above the second chamber, and a second frangible covering being situated below the second chamber;
wherein the second chamber contains a red blood cell flocculant, wherein said red blood cell flocculant is configured to form flocculated red blood cells in the container, wherein said red blood cell flocculant does not form a coagulated mass upon contact with blood in the container; and
wherein the second material is released into the container upon compression of the second compressible button or dimple.

2. The covering and/or lid assembly of claim 1 wherein the blood coagulant material comprises styptic powder.

3. The covering and/or lid assembly of claim 1 comprising a coupling adapter along a perimeter of the lid, said coupling adaptor comprising a threaded configuration suitable for attaching the covering assembly onto a top opening of the container.

4. The covering and/or lid assembly of claim 1 wherein the coagulated mass is a solid mass.

5. The covering and/or lid assembly of claim 1, wherein the frangible covering comprises a foil or plastic film.

6. The covering and/or lid assembly of claim 1, wherein the red blood cell flocculant is polyDADMAC.

7. A collection and disposal system comprising a collection container and a covering and/or lid assembly as defined in claim 1, wherein:
the collection container has a canister configuration and a volume capacity of 100 ml, 250 ml, 500 ml, 1,200 ml or 5000 ml; and
wherein the covering and/or lid assembly comprises a coupling adapter suitable for securely attaching to an opening of the collection container.

8. The collection and disposal system of claim 7, wherein the collection container has a volume of about 1200 ml. or 5000 ml.

9. The collection and disposal system of claim 7 wherein the collection container comprises a surface coating of a second red blood cell flocculant, and wherein the second red blood cell flocculant is configured to form flocculated red blood cells within the collection container.

10. The collection and disposal system of claim 9 wherein the second red blood cell flocculant comprises polyDADMAC.

11. A lid assembly for a container, comprising:
a first compartment, a first compressible button, and a frangible covering, wherein the first compressible button and the frangible covering define the first compartment, wherein the frangible covering is situated below the first compartment;
a blood coagulant material within the first compartment, wherein the blood coagulant material is configured to be selectively released from the first compartment into the container upon compression of the first compressible button, and wherein the blood coagulant material is configured to form a mass of coagulated blood within the container,
a second compartment, a second compressible button, and a frangible covering, wherein the frangible covering is situated below the second compartment; and
a red blood cell flocculant within the second compartment,
wherein the red blood cell flocculant is configured to be selectively released from the second compartment into the container upon compression of the second compressible button, and
wherein the red blood cell flocculant is configured to form flocculated red blood cells within the container, and wherein said red blood cell flocculant does not form a coagulated mass upon contact with blood in the container.

12. The lid assembly of claim 11, wherein the blood coagulant material comprises aluminum chloride, styptic powder, copper sulfate, aluminum sulfate, potassium aluminum, potassium ferrate, ferric sulfate, ferrous sulfate, ferric chloride, or zinc sulfate.

13. The lid assembly of claim 11, wherein the container is a collection canister.

14. The lid assembly of claim 11, wherein the red blood cell flocculant is polyDADMAC.

15. The lid assembly of claim 11, wherein the frangible covering comprises a foil or plastic film.

16. The lid assembly of claim 11, further comprising a coupling adapter along a perimeter of the lid assembly, the coupling adaptor comprising a threaded configuration configured to attach the lid assembly to a top opening of the container.

* * * * *